US006804552B2

(12) United States Patent
Thompson et al.

(10) Patent No.: US 6,804,552 B2
(45) Date of Patent: Oct. 12, 2004

(54) MEMS SWITCHING CIRCUIT AND METHOD FOR AN IMPLANTABLE MEDICAL DEVICE

(75) Inventors: David L. Thompson, Andover, MN (US); Daniel R. Greeninger, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 437 days.

(21) Appl. No.: 10/004,025

(22) Filed: Oct. 31, 2001

(65) Prior Publication Data

US 2002/0095187 A1 Jul. 18, 2002

Related U.S. Application Data

(60) Provisional application No. 60/245,795, filed on Nov. 3, 2000.

(51) Int. Cl.[7] .................................................. A61N 1/00
(52) U.S. Cl. ........................................................ 607/2
(58) Field of Search ...................................... 607/1–114

(56) References Cited

FOREIGN PATENT DOCUMENTS

WO    WO 00/21610    4/2000    ............ A61N/1/39

*Primary Examiner*—Scott M. Getzow
(74) *Attorney, Agent, or Firm*—Girma Wolde-Michael; Michael C. Soldner

(57) ABSTRACT

An improved switching system for use with an implantable medical device (IMD) is described. The system utilizes Micro-Electrical-Mechanical system (MEMs) switches in place of one or more switches formerly implemented using transistor networks. Any type of switching circuit used within an IMD may be implemented using this technology. For example, MEMs switches may be utilized in a circuit for selectably delivering electrical stimulation to a patient, and/ or in a circuit for providing surge protection. The fabrication of the MEMs switches may be performed using one or more separate tubs or wells on a silicon substrate to isolate switching circuitry from other IMD circuitry.

41 Claims, 9 Drawing Sheets

US 6,804,552 B2

MEMS SWITCHING CIRCUIT AND METHOD FOR AN IMPLANTABLE MEDICAL DEVICE

This application claims priority to U.S. Provisional Patent Application No. 60/245,795 filed Nov. 3, 2000, which is incorporated herein by reference in its entirety.

FIELD OF THE INVENTION

This invention relates to an improved system and method for performing switching in an implantable medical device; and more specifically, relates to the use of Micro-Electrical-Mechanical systems (MEMs) technology to implement switching circuitry of an implantable medical device.

BACKGROUND OF THE INVENTION

Many Implantable Medical Devices (IMDs) include circuits for delivering electrical stimulation to tissue. For example, implantable pacing, defibrillation, and cardioversion devices are designed to deliver electrical stimulation to the heart via electrodes that are in contact with cardiac tissue. Other types of implantable devices such as neurostimulation systems are known for delivering electrical stimulation to muscle, nerve, or other types of tissue within a patient's body.

IMDs that deliver electrical stimulation generally include output switching networks to selectively couple stimulation energy to cardiac, muscular, or neurologic tissue from batteries and/or capacitors under supervisory control of algorithms or firmware resident in the device. In the prior art, these switches are generally implemented in CMOS technology using CMOS Field Effect Transistors (FETs). These transistors can be readily implemented in silicon devices using three to five-micron, or larger, CMOS technology. However, as the feature size of the CMOS FETs is decreased below three microns, the breakdown voltage of the FETs is also decreased. If the breakdown voltage decreases to a voltage that is at, or near, the voltage that will be applied across a FET, stimulation pulse parasitic leakage will occur, causing ineffective stimulation, increasing battery current drain, and potentially resulting in damage to the integrated circuit.

One proposed mechanism for solving the above-described problem involves implementing all switching circuitry in at least a three-micron technology in a first integrated circuit, while implementing all other circuitry for the IMD in another integrated circuit employing smaller-sized gates. This type of approach is described in U.S. Pat. No. 5,833,710 to Jacobson. This proposed solution adds an additional integrated circuit to the design, increasing system size and cost. Moreover, this method requires the addition of hybrid circuit interconnects to couple the multiple integrated circuits. These interconnections are costly to manufacture and are prone to failure. Also, interconnections on the hybrid circuit level generally consume more current than interconnections contained within a single integrated circuit.

Another solution to the problem involves employing several FET transistors in series in place of a single FET to implement a switching function. This allows a given voltage drop to be shared by multiple transistors such that the likelihood of circuit damage and/or leakage is decreased. However, this solution has the disadvantage of greatly increasing the amount of silicon area required to implement each switch. Additionally, the design is complicated because the multiple FETs implementing a single switch must be enabled in a predetermined order to prevent the full voltage drop from being experienced by a single FET even for a very brief period, since this could damage the circuit or cause large leakage currents. The implementation of this design approach therefore generally results in the use of a significantly increased silicon die area.

Yet another approach is discussed in U.S. Pat. No. 5,097,830 to Eikefjord, et al. This patent describes an external defibrillator that incorporates transfer relays to deliver the defibrillation pulse to a patient. This design consumes a relatively large amount of space.

While the above discussion focuses on switching networks used within output circuitry of an IMD, those skilled in the art will recognize that other switches in an IMD are associated with problems similar to those discussed above. What is needed, therefore, is an improved switching system and method for use in implementing any switching function within an IMD that can be robustly implemented using a substantially smaller die area.

SUMMARY OF THE INVENTION

The current invention involves an improved switching system for use with an implantable medical device (IMD). The system utilizes Micro-Electrical-Mechanical system (MEMs) switches in place of one or more switches conventionally implemented using transistor networks. These MEMs switches provide electrical and mechanical coupling between two terminals of a circuit. These switches, which have dimensions in a range of less than 10 microns, can be manufactured on conventional integrated circuit dies. Because these MEMs switches are capable of sustaining a much larger voltage across the switch terminals than are conventional switches implemented using transistor networks, the resulting circuit is more reliable, and the switching circuit and control logic may be simplified. This minimizes the die area required to implement the system. If desired, an entire IMD including switching circuitry may be implemented using a single integrated circuit die.

According to one aspect of the system, the fabrication of the MEMs switches may be performed using one or more separate tubs or wells on a silicon substrate. This isolates switching circuitry from other IMD circuitry. As such, switching circuitry implemented using three to five micron technology may reside on the same substrate as transistors that are implemented using smaller technology. Isolating the circuits in this manner minimizes substrate crosstalk, breakdown, heating, and circuit latch-up concerns. This approach could also be used to isolate RF or noise-sensitive circuitry.

Various types of switches may be implemented using MEMs technology, including latching and momentary-contact switches. The switches may be activated using various types of activation mechanisms including electrical, electromagnetic, and thermal signals. These switches may be fabricated using any of the known fabrication techniques, including the Lithographie, Galvanoformung, Abformung (LIGA) method.

According to one embodiment, the invention involves an IMD that is capable of providing electrical stimulation to a patient where the output switches are implemented using MEMs switch technology. In another embodiment, the invention involves an IMD including a first circuit that is capable of providing electrical stimulation to a patient, and a switching circuit including a MEMs switch that selectively allows the electrical stimulation to be routed to the desired electrode pair or configuration on the patient. The first circuit may be a circuit to deliver pacing pulses, may be a high-voltage output circuit as may be included in a defibrillation system, may involve a neurostimulator, or another type of treatment mechanism.

In a further embodiment the output circuit implemented in the IMD may include a return current path that is selectable using switches implemented using MEMs technology. In an additional embodiment, the IMD may include a surge protection circuit implemented using MEMs technology, where a switch or switches may open upon sensing a condition that may damage the implanted device. In yet another embodiment, the invention may include a MEMs switch or switches used to selectively apply power to one or more circuits in an IMD.

According to one aspect of the invention, a method of controlling delivery of electrical stimulation to a body is provided, including the steps of generating a stimulation signal, and utilizing a MEMs switch to control delivery of that stimulation signal to the body. The MEMs switch may be controlled using any of the mechanisms described above, including electrical, electromagnetic, and thermal control systems.

Additional objects, features, and advantages of the present invention will become apparent from the description and the related drawings, and from the claims.

BRIEF DESCRIPTION OF THE DRAWINGS

FIG. 7b is a top view of the integrated circuit of FIG. 7a.

DETAILED DESCRIPTION OF THE DRAWINGS

Figure 1:
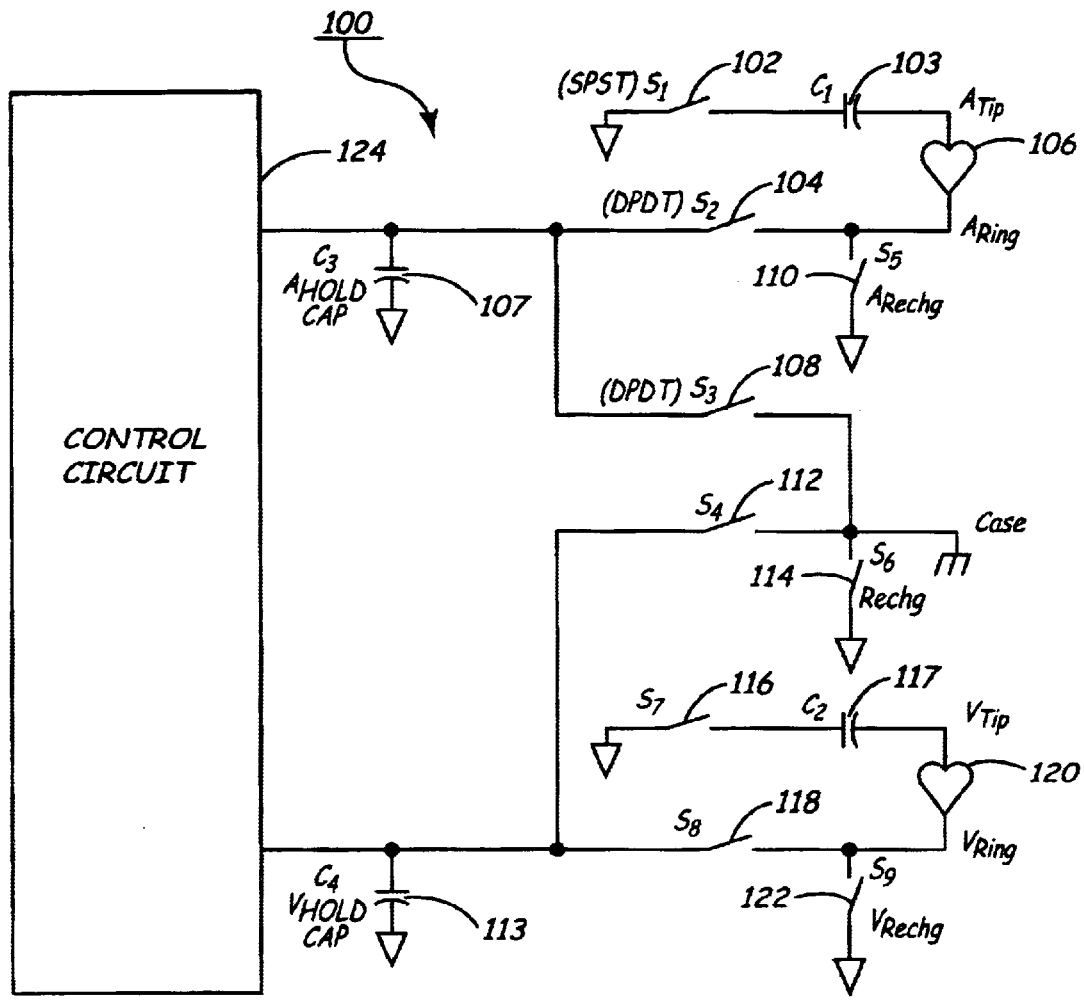
FIG. 1 is a block diagram illustrating a typical prior art switching network used in implantable medical devices.

FIG. 1 is a block diagram illustrating a typical prior art switching network 100 used in implantable medical devices. Switches S1 102 and S2 104 provide atrial bipolar pacing pulses to the atrial chamber 106 of the heart. The stimulation pulse is coupled to the heart via a coupling capacitor 103 from an atrial holding capacitor 107. Similar switches S7 116 and S8 118 provide ventricular bipolar pacing pulses to the ventricular chamber 120 of the heart. These ventricular stimulation pulses are delivered from ventricular holding capacitor 113 via coupling capacitor 117.

Control circuit 124 controls the closure of all switches as well as the voltage levels on holding capacitors 107 and 113. Switches 110 and 122 are closed after the atrial or ventricular stimulation pulses, respectively, have been delivered to allow for the discharge of residual charge residing on capacitors 103 and 117, as well as any charge accumulated at the electrode-tissue interface. Switches 108 and 112 allow unipolar pacing of the atrial and/or ventricular chamber of the heart. Switch 114 allows discharge of capacitors 103 and 117 when pacing in the unipolar mode.

Figure 2:
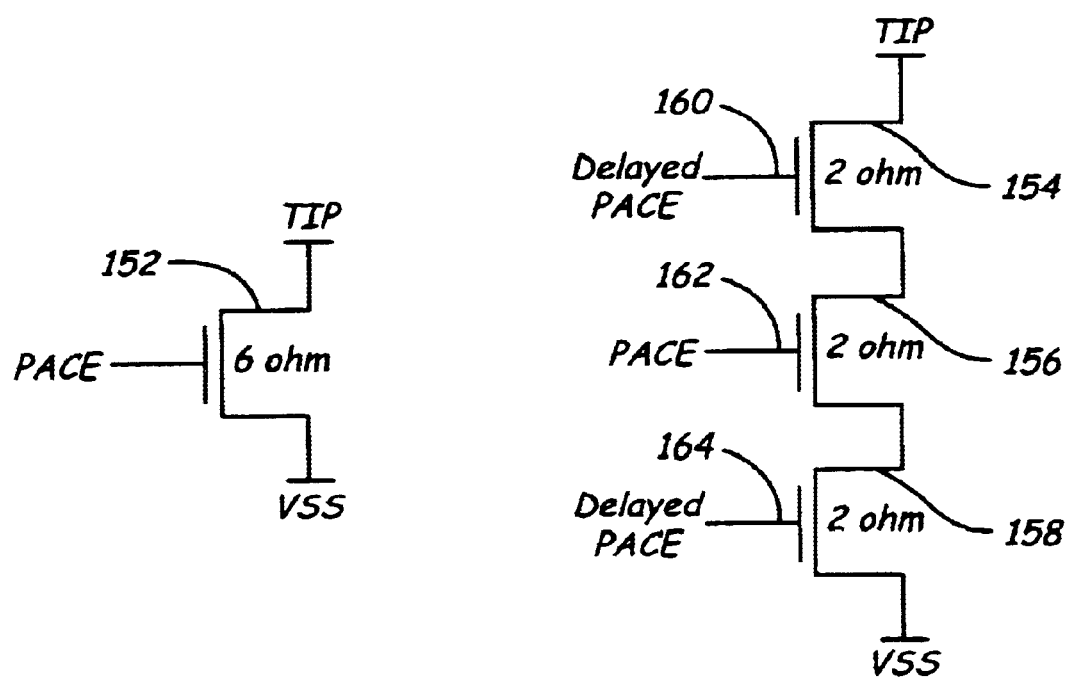
FIG. 2 is a block diagram of an alternative prior art switching network.

FIG. 2 is a block diagram of an alternative prior art switching network. Three two-ohm FETs 154, 156, and 158 are placed in series to replace a single six-ohm FET 152. Any voltage drop is distributed across the three transistors so that the likelihood of circuit damage and/or leakage is decreased. As discussed above, this solution undesirably increases the amount of silicon area required to implement each switch. Additionally, the control logic associated with the switch must be more complex, since the FETs must be enabled in an appropriate sequence to prevent circuit damage. Lastly, crosstalk, or signal pickup from the pacing switches to more sensitive areas of an IC or substrate (i.e. sense amplifiers) may be problematic.

Figure 3:
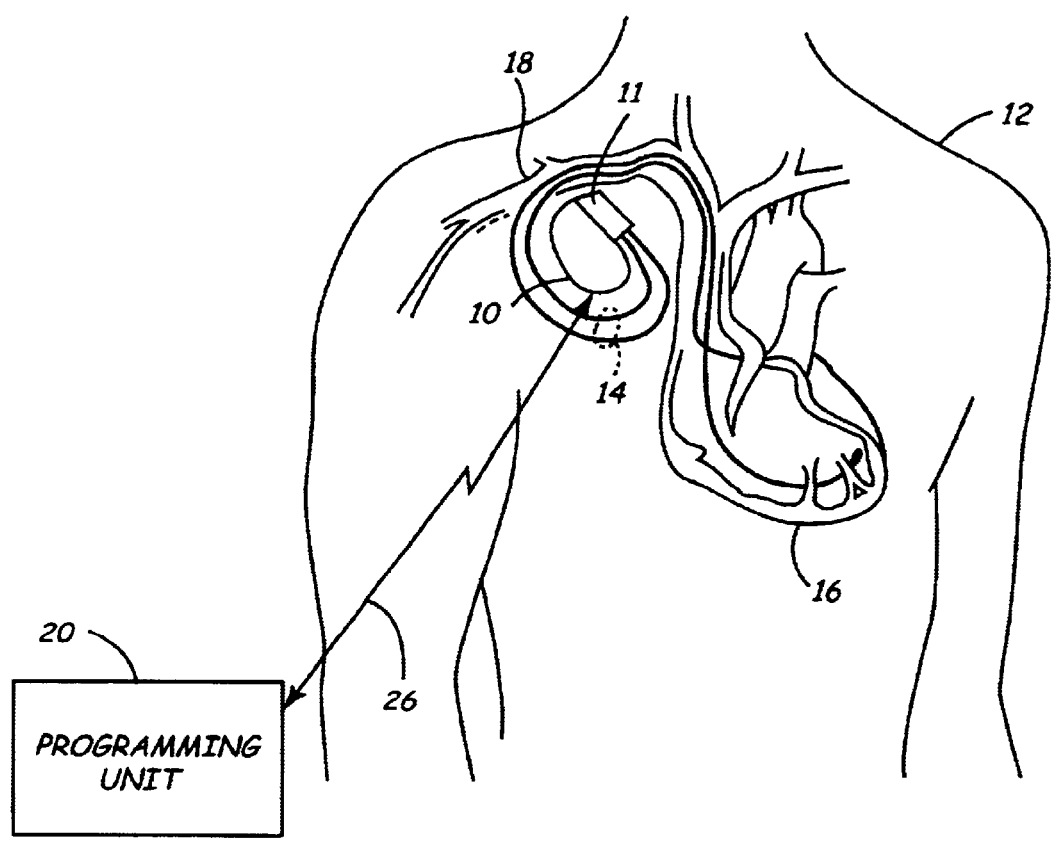
FIG. 3 is a block diagram of an implantable medical device (IMD) that may be adapted to employ the switching system of the present invention.

FIG. 3 is a block diagram of an implantable medical device (IMD) that may be adapted to employ the switching system of the present invention. Exemplary IMD 10 is shown as a pacemaker implanted in a patient 12. In accordance with conventional practice in the art, pacemaker 10 is housed within a hermetically sealed, biologically inert outer casing, which may itself be conductive so as to serve as an indifferent electrode in a pacing/sensing circuit. One or more pacemaker leads 14 are electrically coupled to IMD 10 in a conventional manner and extend into the patient's heart 16 via a vein 18. Disposed generally near the distal end of leads 14 are one or more exposed conductive electrodes for receiving electrical cardiac signals and/or for delivering electrical pacing stimuli to heart 16. As will be appreciated by those of ordinary skill in the art, the electrodes of leads 14 may be positioned in the atrium and/or ventricle of heart 16. An external programmer 20 is provided for non-invasive communication with IMD 10 via uplink and downlink communication channel 26.

Figure 4:
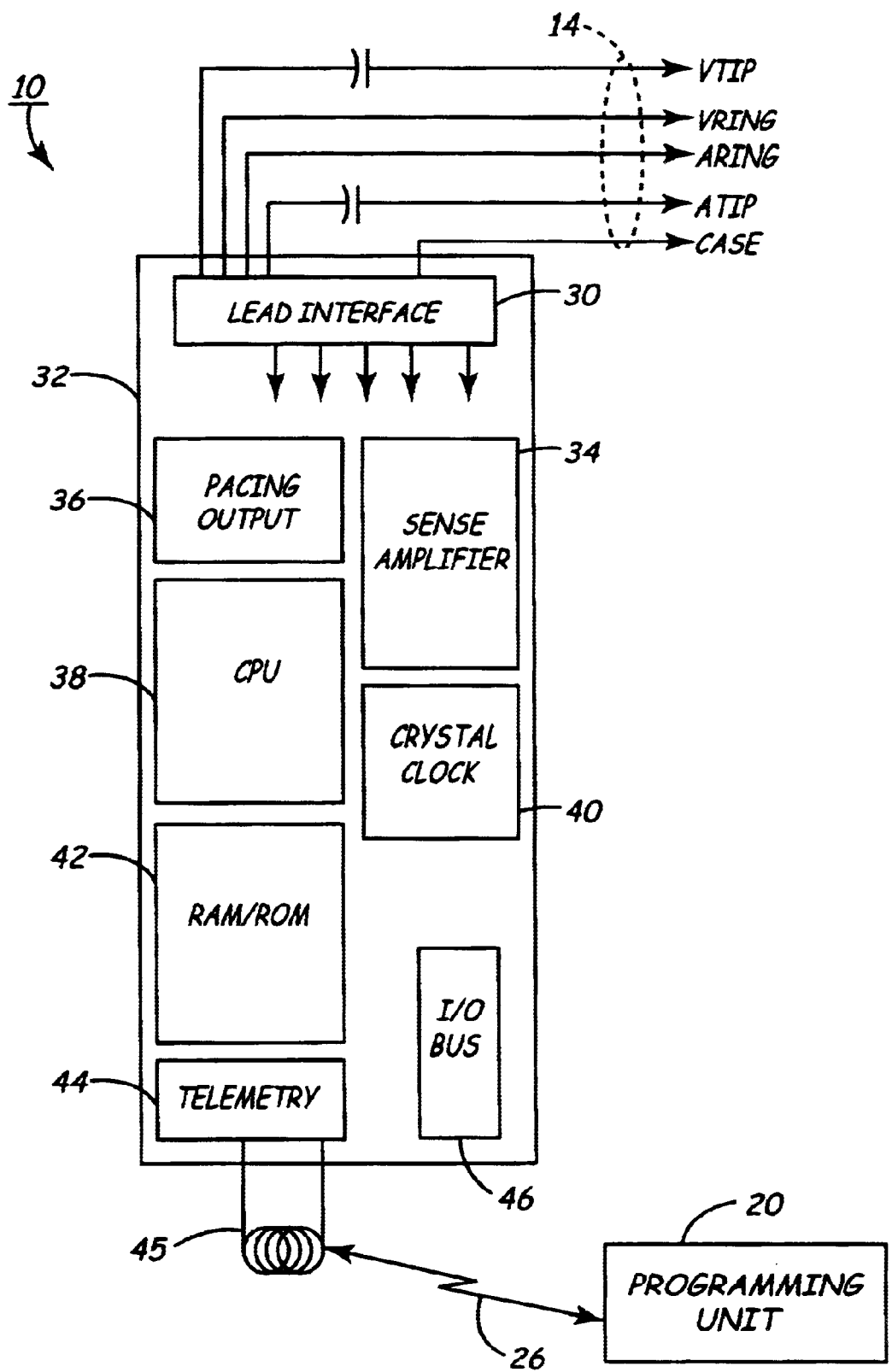
FIG. 4 is a block diagram of an electronic circuitry that may be utilized within an implantable medical device such as a pacemaker in accordance with the presently disclosed invention

FIG. 4 is a block diagram of electronic circuitry that may be utilized within an implantable medical device such as a pacemaker in accordance with the presently disclosed invention. Pacemaker 10 comprises a stimulation control circuit 32 for controlling pacing and sensing functions. Stimulation control circuit 32 may be of conventional design such as disclosed in U.S. Pat. No. 5,052,388 issued to Sivula et al. For example, this circuit may include sense amplifier circuitry 34, stimulating pulse output circuitry 36, a crystal clock 40, a random-access and/or read-only memory (RAM/ROM) unit 42, an I/O Bus 46, and a central processing unit (CPU) 38, all of which are well-known in the art. A communication circuit such as telemetry system 44 may be provided to allow the device to communicate with external programmer 20 via antenna 45 and communication channel 26.

Pacemaker 10 may be coupled to one or more leads 14 that extend transvenously into the patient's heart 16 or associated vascular system. These leads may be connected to the internal circuitry of pacemaker 10 via a standard or nonstandard connector block assembly 11, as shown in FIG. 3. The lead conductors may be electrically coupled with the internal electrical components of pacemaker 10 via a lead interface circuit 30. This interface circuit may be designed to function as a switch to selectively and dynamically establish necessary connections between the circuitry of pacemaker 10 and the various conductors of leads 14, including atrial tip and ring (ATIP and ARING) electrode conductors, and ventricular tip and ring (VTIP and VRING) electrode conductors. For the sake of clarity, the specific connections between leads 14 and the various components of pacemaker 10 are not shown in FIG. 4. However, it will be clear to those of ordinary skill in the art that leads 14 will necessarily be coupled, either directly or indirectly, to sense amplifier circuitry 34 and stimulating pacing output circuit 36.

As previously noted, stimulation control circuit 32 includes central processing unit (CPU) 38 which may be an off-the-shelf programmable microprocessor, a microcontroller, or a custom integrated circuit. CPU 38 executes programmed instructions stored in RAM/ROM unit 42 to control the timed operation of pacing output circuit 36 and sense amplifier circuit 34. Pacing output circuit 36, which generates cardiac stimuli signals, may be of the type disclosed in U.S. Pat. No. 4,476,868 to Thompson incorporated herein by reference in its entirety. Alternatively, any other type of pacing output circuit known in the art may be adapted within the system.

Sense amplifier circuit 34 receives electrical cardiac signals from leads 14. These signals are processed to detect the occurrence of specific cardiac electrical events, including atrial contractions (P-waves) and ventricular contractions (R-waves). Sense amplifier circuit 34 then provides event-indication signals to CPU 38 for use in controlling the synchronous stimulating operations of pacemaker 10 in accordance with common practice in the art. In addition, these event-indication signals may be stored as diagnostic data in RAM/ROM 42 and subsequently communicated via uplink transmission 26 to an external programmer 20.

Control circuit 32 further includes crystal oscillator circuit 40 to provide clock signals for control circuit 32. Other components and subsystems may be provided within the scope of the current invention, including activity sensors and/or any other type of subsystem known for use within an IMD. The various components are powered by a power source such as a battery (not shown) that is contained within the hermetic enclosure of pacemaker 10 in accordance with common practice in the art.

Figure 5:
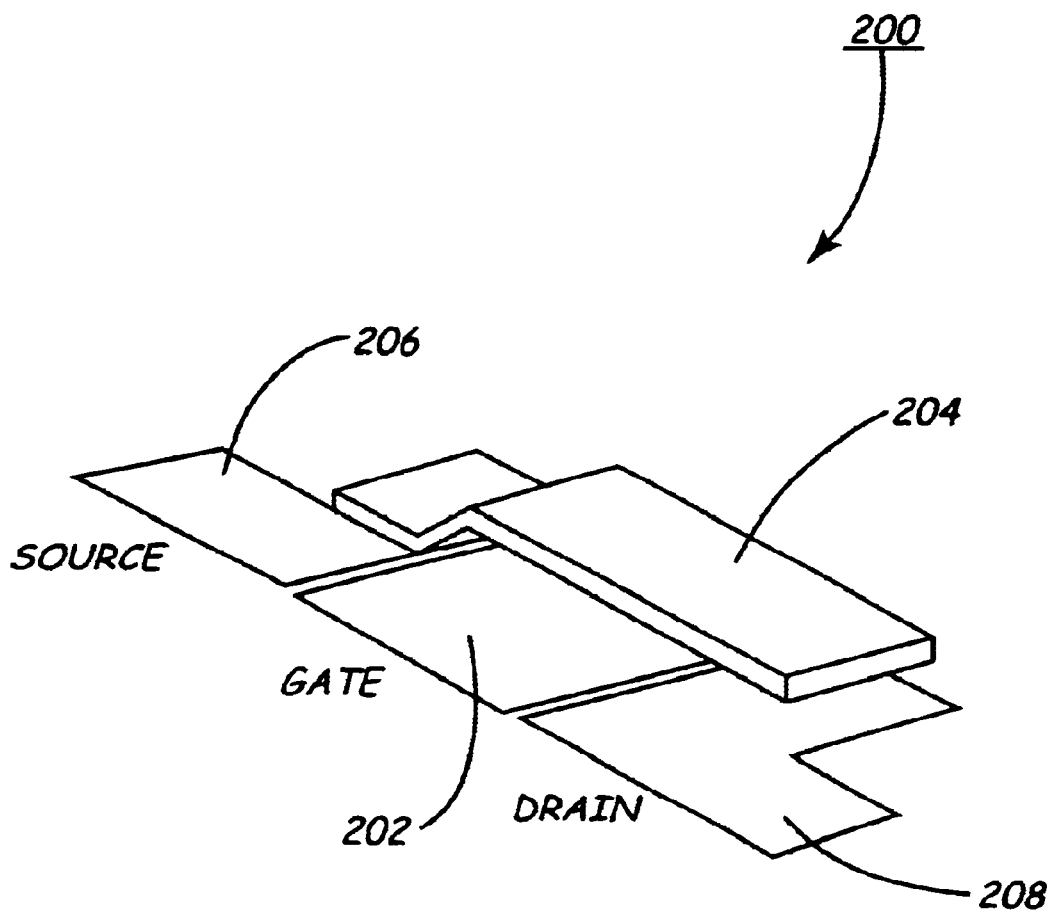
FIG. 5 is a functional block diagram of a switch implemented using Micro-Electrical-Mechanical systems (MEMs) technology as is employed by the current invention.

FIG. 5 is a functional block diagram of a switch implemented using Micro-Electrical-Mechanical systems (MEMs) technology as is employed by the current invention. This technology allows mechanically-operable switches to be implemented using conventional CMOS technology. MEMs switches may be fabricated using a technique called Lithographie, Galvanoformung, Abformung (LIGA), as is described in U.S. Pat. No. 5,190,637 to Guckel incorporated herein by reference in its entirety. Alternatively, or additionally, the above-described embodiments may be fabricated in bulk using standard silicon micro-machining processes. These MEMs switches are capable of sustaining a much larger voltage across the switch terminals than are conventional switches implemented using transistor networks.

During operation, a voltage is applied to gate 202. This creates an electrostatic force that pulls a conductive member 204 into contact with both a source terminal 206 and a drain terminal 208. In this position, the switch in "closed", creating a conduction path between the source and drain terminals. In one embodiment, the conductive member 204 is mechanically and electrically coupled to the source 206, and is further electrically coupled to the drain 208 when a voltage is applied to gate 202. This type of switch may be implemented using a cantilevered beam design such as described in U.S. Pat. No. 4,674,180 to Zavracky, et al., incorporated herein by reference in its entirety. In another embodiment, the conductive member may be mechanically and electrically coupled to the drain 208, and electrically coupled to the source 206 when a voltage is applied to gate 202.

Although the switches of FIG. 5 are actuated by applying a voltage on the drain terminal, the actuation method may alternatively be electromagnetic or thermal. For example, electromagnetically-actuated micromechanical multicontact relays are disclosed by Taylor et al. in the article entitled "Integrated Magnetic Microrelays: Normally Open, Normally Closed, and Multi-Pole Devices" (Proc. IEEE Transducers '97 International Conference on Solid-State Sensors and Actuators, Chicago, Ill. Jun. 16–19, 1997), incorporated herein by reference in its entirety. Alternatively, U.S. Pat. No. 5,994,816 to Dhuler, incorporated herein by reference in its entirety, describes a thermally-activated switch that may be alternatively employed by the current invention.

According to one embodiment of the invention, MEMs switches may be utilized in pacing output circuits as discussed above. Specifically, any or all of the switches shown in FIG. 1 may be replaced with MEMs switches. For example, switches 102, 110, 114, 116, and 122 may be single-pole, single-throw (SPST) momentary contact switches. Switches 104/108 and 112/118 may be double-pole, double-throw (DPDT) latching switches allowing permanently programmable unipolar or bipolar pacing configuration. These switches may also be used to implement protection circuits that may be employed instead of Zener diodes to protect sensing circuitry against high-voltage surges.

Through use of MEMs switches, the output system is more reliable, less costly, and results in a much smaller integrated circuit die area so that the overall volume of the IMD may be reduced. The use of MEMs switches may allow the use of smaller geometry integrated circuits for the remaining IMD circuitry. Furthermore, because the MEMs switches can be implemented in a small area, many switches can be incorporated into a single device. For example, a multisite 3- and 4-chamber pacemaker may be implemented easily on a single die. Exemplary devices are described in U.S. Pat. Nos. 6,070,101, 6,081,748, 6,122,545, and 6,148,234 incorporated herein by reference in their entireties.

Figure 6A:
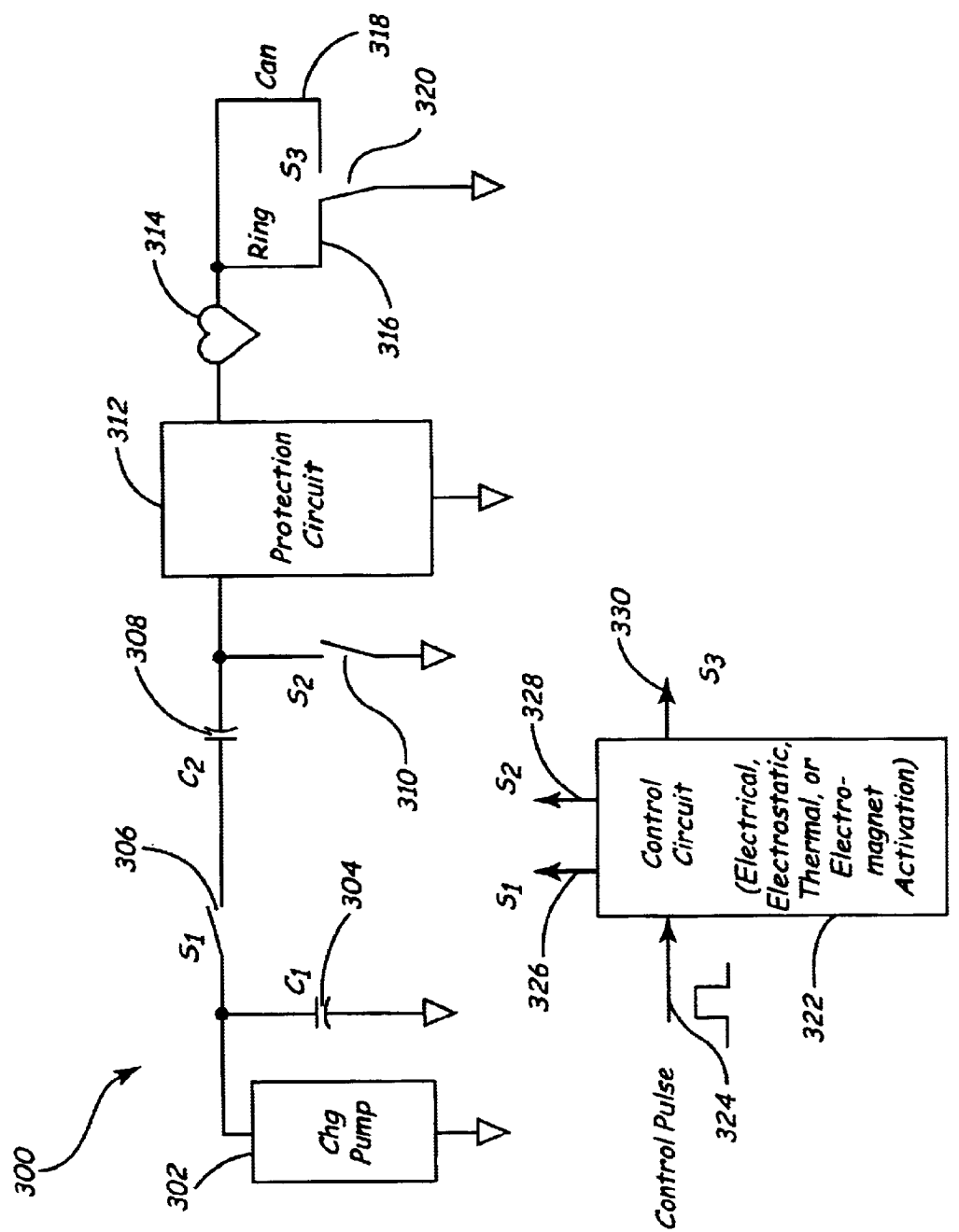
FIG. 6a is a circuit diagram illustrating one embodiment of an output circuit according to the current invention.

FIG. 6a is a circuit diagram illustrating one embodiment of an output circuit 300 according to the current invention. This embodiment incorporates a device protection circuit 312. Charge pump 302 and capacitor 304 store a preprogrammed output charge. This output charge may be a high-voltage charge as is used within a cardioversion or defibrillation system, or could be an output charge used in a pacing application. A control pulse 324 is delivered via control circuit 322 and control line 326 to close switch 306. As noted above, this control circuit 322 could be adapted to provide electromagnetic or thermal activation signals if electromagnetically or thermally-activated MEMs switches are utilized instead of electrically-activated MEMs switches. Additionally, the control circuit may operate based, in part, on physiological signal measurements obtained from the body, including EGM, pressure, temperature, blood flow, or any of the other physiological signal measurements acquired using sensing devices known in the art.

After the switch is closed, the charge stored on capacitor 304 is delivered to the heart 314 via coupling capacitor 308 and protection circuit 312. The return current path is selectably provided by ring 316 or can 318 based on the positioning of switch 320, which may be controlled by control line 330 of control circuit 322. After delivery of the pacing pulse, switch 310 may be closed for 5 to 10 millisecond to discharge the lead/tissue interface polarization voltage, as controlled by control line 328.

Figure 6B:
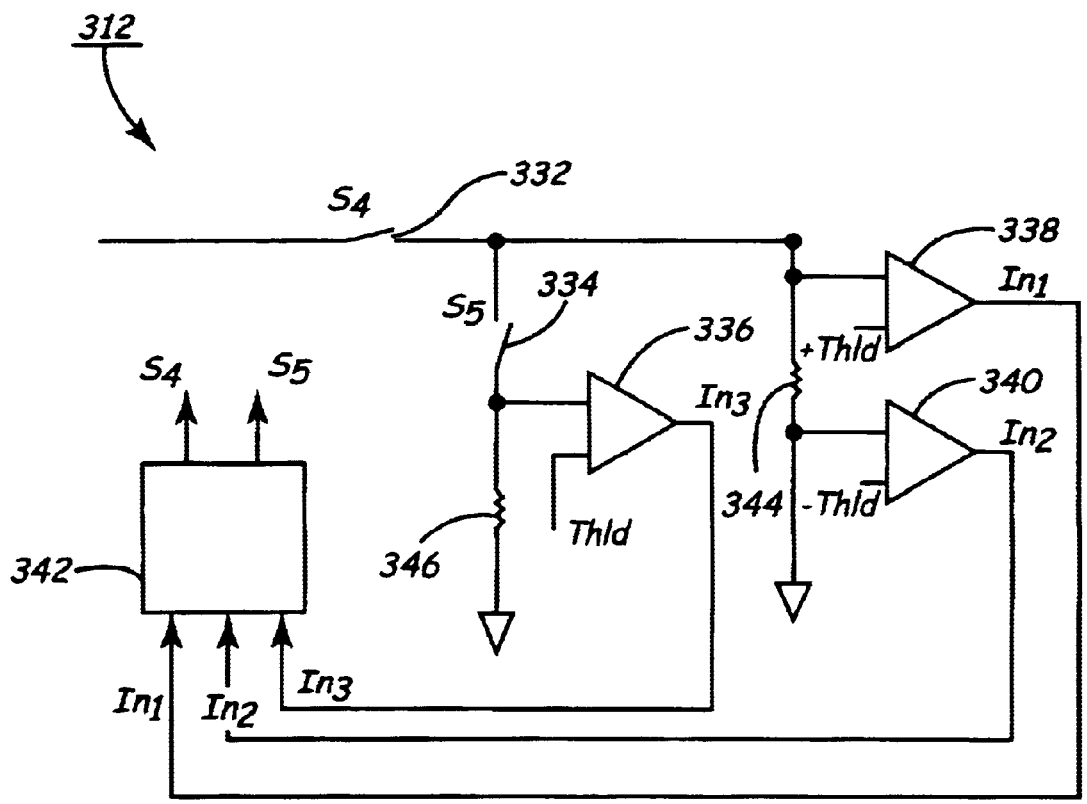
FIG. 6b is a circuit diagram illustrating one embodiment of a protection circuitry as may be used within the current invention.

FIG. 6b is a circuit diagram illustrating one embodiment of protection circuitry 312. During normal operation, series switch 332 is closed to allow pacing pulses to stimulate the heart 314. During large signal perturbations on the lead system 14, a voltage is applied to positive and negative comparators 338 and 340, respectively. If a large voltage is sensed across the resistor 344, one of the comparators will switch depending upon the polarity of the input signal. Protection control circuit 342 will, in turn, cause switch 332 to open and switch 334 to close providing protection to IMD 10. Current flow through resistor 346 and closed switch 334 will allow comparator 336 to latch the protection control circuit in this mode until the signal is removed.

According to yet another embodiment of the current invention, MEMs fabrication technology may be implemented using a separate tub on the silicon substrate. This would isolate the output circuitry, including the MEMs components, from the other IMD circuitry. As such, the output technology, which is implemented using three to five micron technology, may reside on the same substrate as the smaller transistors utilized for the other circuitry. Isolating the circuits in this manner would minimize substrate crosstalk, breakdown, heating, and circuit latch-up concerns. Additionally, this approach could be used to isolate RF transmit or receive telemetry circuitry or other noise-sensitive circuitry.

Figure 7A:
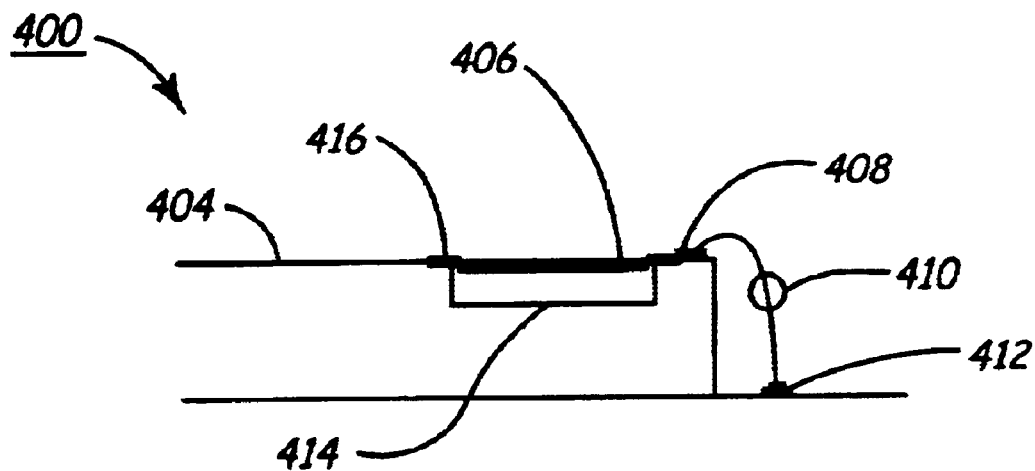
FIG. 7a is a side view of an integrated circuit employing a separate tub to isolate output circuitry from the rest of the IMD circuitry.

FIG. 7a is a side view 400 of an integrated circuit (IC) 404 wherein a separate tub or well 414 is used to isolate output circuitry 406 from the rest of the IMD circuitry. Bridges 416 provide mechanical connection and support to isolated circuitry 406. The bridges are coupled to IC bonding pads 408, which are, in turn, coupled to substrate bonding pads 412 via wire bonds 410. Electrical conductors 418 provide signal and power interconnections from the IC 404. Methods of manufacturing an IC to incorporate a component floating above a well in this manner are described in U.S. Pat. Nos. 5,825,092, 5,874,883, 5,396,101 and 5,539,241, and in the publication entitled "Processing Scheme Creates Silicon Voids as an Alternative to SOI", D Bursky, Electronic Design, Dec. 17, 1999, Pg 34, all of which are incorporated herein by reference in their entireties.

Figure 7B:
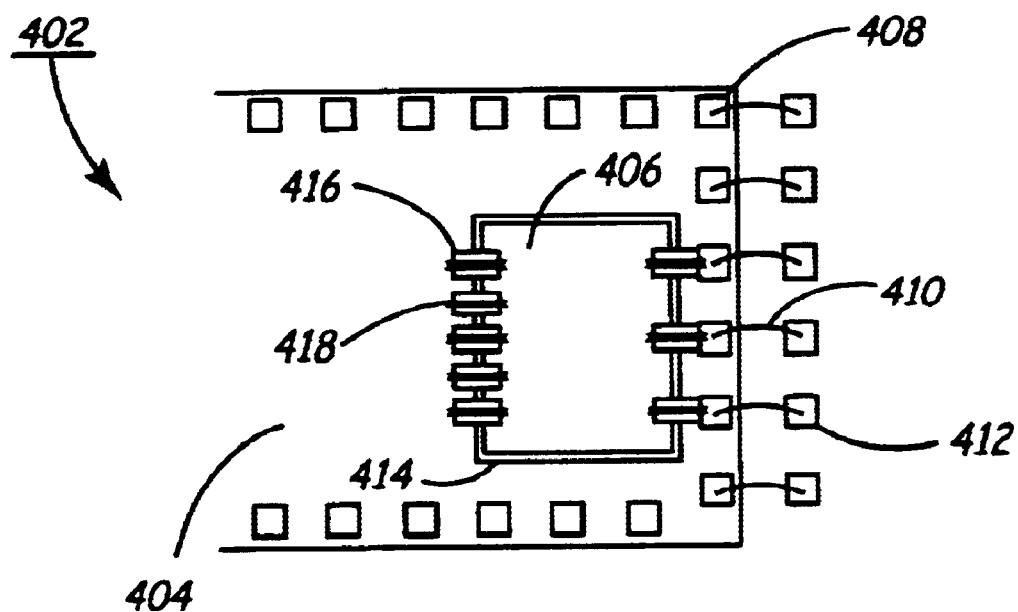

FIG. 7b is a top view 402 of the integrated circuit of FIG. 7a. This view more clearly illustrates bridges 416 and electrical conductors 418, as well as interconnection wire bonds 410.

In another embodiment of the invention, only protection circuitry could be isolated from other circuitry in a separate tub. In yet another embodiment, each individual switch may be isolated in a respective tub. This approach could be particularly useful for those switches that will potentially be exposed to larger voltages.

Figure 8:
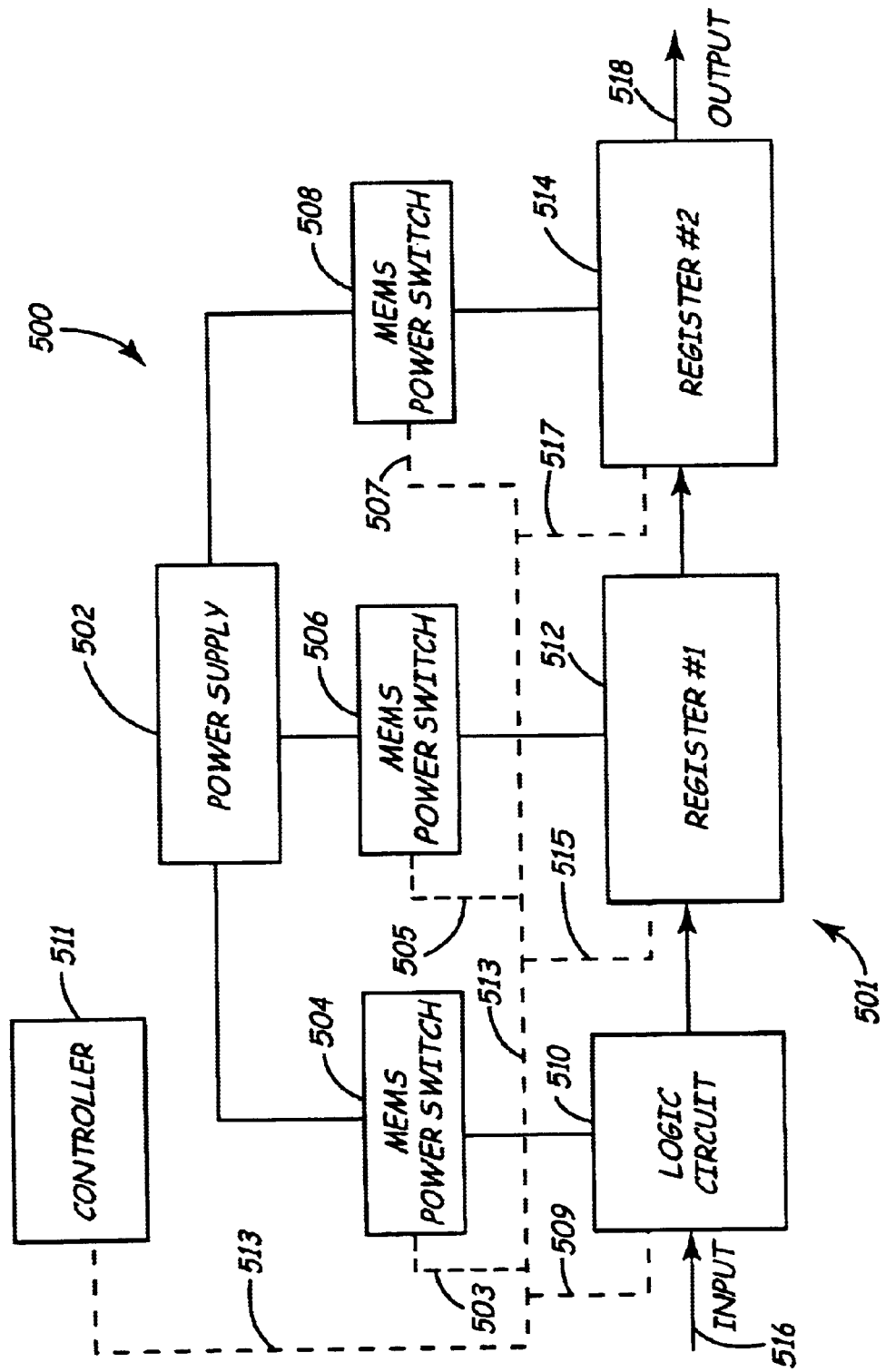
FIG. 8 is an illustrative block diagram depicting switches for selectively applying and removing power to various digital components in accordance with one embodiment of the current invention.

FIG. 8 is a block diagram illustrating another embodiment of the present invention. This figure includes a MEMs switch or switches used to selectively apply power to one or more circuits in an IMD. A method and apparatus for selectively powering circuits in an IMD using standard CMOS switches is described in U.S. Pat. No. 5,916,237 to Schu, incorporated herein by reference in its entirety. One issue with inserting a switch in series with a voltage supply is that the voltage drop created by current through the $R_{on}$ impedance of the switch may affect the circuit that is being powered. Because MEMs switches make a direct mechanical connection, their $R_{on}$ impedance is much lower than a typical CMOS switch used for this purpose. The voltage drop across the switch is significantly reduced through the use of MEMs switches. In addition, significant silicon area savings may be realized by integrating MEMs switches to power-down circuits that are not being used.

In FIG. 8, a digital circuit 501 includes a number of MEMs power switches 504, 506, 508 that are controlled by controller 511, which may be a microprocessor or other programmable control device. Many of the elements of circuitry 500 shown in FIG. 8 are intended to represent circuitry typically found in a wide variety of implantable medical devices. Input signals are provided on input signal or bus 516, and output signals are presented on output signal or bus 518. Power provided by power supply 502 is selectively applied to, and removed from, various circuit elements such as logic circuit 510, or registers 512 and 514 of digital circuit 501 in a coordinated manner between controller 511 and MEMs power switches 504, 506, and 508. Control bus 513 contains a group of power control lines 503, 505, and 507, which control the MEMs power switches, as well as a group of enable control lines 509, 515, and 517 which enable and/or disable the logic blocks as part of the power down or power up procedure.

Although the foregoing description utilizes a pacing device for exemplary purposes, the present invention may be employed by any type of IMD, including, but not limited to, defibrillators, cardioverters, neurostimulators, and the like. In particular, high-voltage MEMs switches may be used to deliver therapy from a cardioverter/defibrillator. Moreover, while the present invention has been illustrated and discussed in terms of the above-described embodiments, it should be understood that the scope of the invention is not to be limited to these exemplary embodiments. Rather, variations of the particular embodiments described herein will occur to those of ordinary skill in the art and yet be within the scope of the invention. Therefore, the scope of the invention is to be defined only by the following claims.

What is claimed is:

1. An implantable medical device (IMD), comprising:
   a first circuit adapted to perform a first function;
   a second circuit adapted to perform a second function; and
   a switching circuit coupled to the first and second circuits to selectively electrically couple the first circuit to the second circuit, the switching circuit comprising at least one Micro-Electrical-Mechanical System (MEMs).

2. The IMD of claim 1, wherein the first circuit comprises a circuit to supply electrical charge, and the second circuit comprises a circuit to deliver the electrical charge to a body.

3. The IMD of claim 1, wherein the first circuit comprises a source of electrical power.

4. The IMD of claim 3, wherein the second circuit comprises a circuit to receive the electrical power.

5. The IMD of claim 1, wherein the switching circuit includes a circuit to selectively electrically isolate the first circuit from the second circuit to prevent the second circuit from voltage surges experienced by the first circuit.

6. The IMD of claim 5, wherein the switching circuit is substantially suspended above the different one of the multiple wells.

7. The IMD of claim 1, wherein the second circuit is adapted to provide at least one return current path for the first circuit.

8. The IMD of claim 1, wherein the Micro-Electrical-Mechanical System includes an activation mechanism that is electromagnetically activated.

9. The IMD of claim 1, wherein the Micro-Electrical-Mechanical System includes an activation mechanism that is thermally activated.

10. The IMD of claim 1, wherein at least one of the first and second circuits is adapted to provide high-voltage electrical stimulation to a body.

11. The IMD of claim 1, wherein the first circuit comprises multiple medical electrical leads, the second circuit comprises a circuit to generate an electrical signal, and wherein the switching circuit includes a circuit to route the electrical signal to the multiple medical electrical leads.

12. The IMD of claim 1, wherein the MD is implemented using a single integrated circuit die including multiple wells, and wherein at least one of the first and second circuit is implemented in one of the multiple wells, and the switching circuit is implemented using a different one of the multiple wells.

13. An implantable medical device (IMD), comprising
a first circuit that is capable of providing electrical stimulation to a patient; and
a switching circuit coupled to the first circuit to selectively allow the electrical stimulation to be provided to the patient, the switching circuit comprising a Micro-Electrical-Mechanical system (MEMs).

14. The IMD of claim 13, and further including a control circuit coupled to the switching circuit to control the switching circuit such that the electrical stimulation is selectively provided to the patient.

15. The IMD of claim 14, and further including a surge protection circuit coupled to the first circuit.

16. The IMD of claim 15, wherein the surge protection circuit comprises a Micro-Electrical-Mechanical system (MEMs).

17. The MD of claim 13, wherein the MD is implemented using a single integrated circuit die including multiple wells, and wherein the first circuit is implemented in one of the multiple wells, and the switching circuit is implemented using a different one of the multiple wells.

18. The IMD of claim 17, wherein the switching circuit is substantially suspended above the different one of the multiple wells.

19. The IMD of claim 13, wherein the control circuit provides at least one electrical signal to control the switching circuit.

20. The IMD of claim 13, wherein the Micro-Electrical-Mechanical system includes an activation mechanism that is electromagnetically activated.

21. The IMD of claim 13, wherein the Micro-Electrical-Mechanical system includes an activation mechanism that is thermally activated.

22. The IMD of claim 13, wherein the switching circuit includes a MEMs switch to select a return current path.

23. The IMD of claim 13, wherein the first circuit is capable of delivering high-voltage electrical stimulation.

24. The IMD of claim 13, wherein the stimulation circuit includes a circuit to deliver high-voltage electrical stimulation.

25. The IMD of claim 13, wherein the Micro-Electrical-Mechanical system is a latching switch.

26. The IMD of claim 13, wherein the Micro-Electrical-Mechanical system is a momentary-contact switch.

27. A method of controlling delivery of electrical stimulation to a body, comprising:
 a.) generating a stimulation signal; and
 b.) utilizing a Micro-Electrical-Mechanical system (MEMs) switch to control delivery of the stimulation signal to the body.

28. The method of claim 27, wherein step b.) comprises generating an electrical control signal to close the MEMs switch.

29. The method of claim 27, wherein step b.) comprises generating an electromagnetic control signal to close the MEMs switch.

30. The method of claim 27, wherein step b.) comprises generating a thermal control signal to close the MEMs switch.

31. The method of claim 27, wherein the stimulation signal is a high-voltage stimulation signal.

32. The method of claim 27, wherein the stimulation signal is a pacing signal.

33. The method of claim 27, and further comprising utilizing a MEMs switch to select a return current path.

34. The method of claim 27, and further comprising:
 detecting an electrical disturbance; and
 utilizing a MEMs switch to manage the electrical disturbance.

35. A method of operating an implantable medical device, comprising:
 (a) providing a first circuit adapted to perform a first function;
 (b) providing a second circuit adapted to perform a second function; and
 (c) utilizing at least one Micro-Electrical-Mechanical System (MEMs) to selectively electrically couple the first and second circuits.

36. The method of claim 35, and further comprising utilizing the first circuit to deliver power to the second circuit after the first and second circuits are selectively electrically coupled.

37. The method of claim 35, and further comprising utilizing at portion of the second circuit as a return current path for the first circuit after the first and second circuits are selectively electrically coupled.

38. The method of claim 35, wherein step (c) comprises electrically isolating the first circuit from the second circuit when a electrical disturbance is sensed in at least one of the first and the second circuits.

39. The method of claim 35, wherein step (c) comprises utilizing an electromagnetic signal to cause the MEMs to electrically couple the first and second circuits.

40. The method of claim 35, wherein step (c) comprises utilizing a thermal signal to cause the MEMs to electrically couple the first and second circuits.

41. The method of claim 35, and further comprising utilizing the first and second circuits to deliver electrical stimulation to a patient.

* * * * *

UNITED STATES PATENT AND TRADEMARK OFFICE
CERTIFICATE OF CORRECTION

PATENT NO. : 6,804,552 B2 Page 1 of 1
APPLICATION NO. : 10/004025
DATED : October 12, 2004
INVENTOR(S) : David L. Thompson et al.

It is certified that error appears in the above-identified patent and that said Letters Patent is hereby corrected as shown below:

Column 9, line 15, delete "the MD is" and insert --the IMD is--

Column 9, line 37, delete "the MD of" and insert --the IMD of--

Signed and Sealed this

Twenty-sixth Day of December, 2006

JON W. DUDAS
*Director of the United States Patent and Trademark Office*